Figure 1:
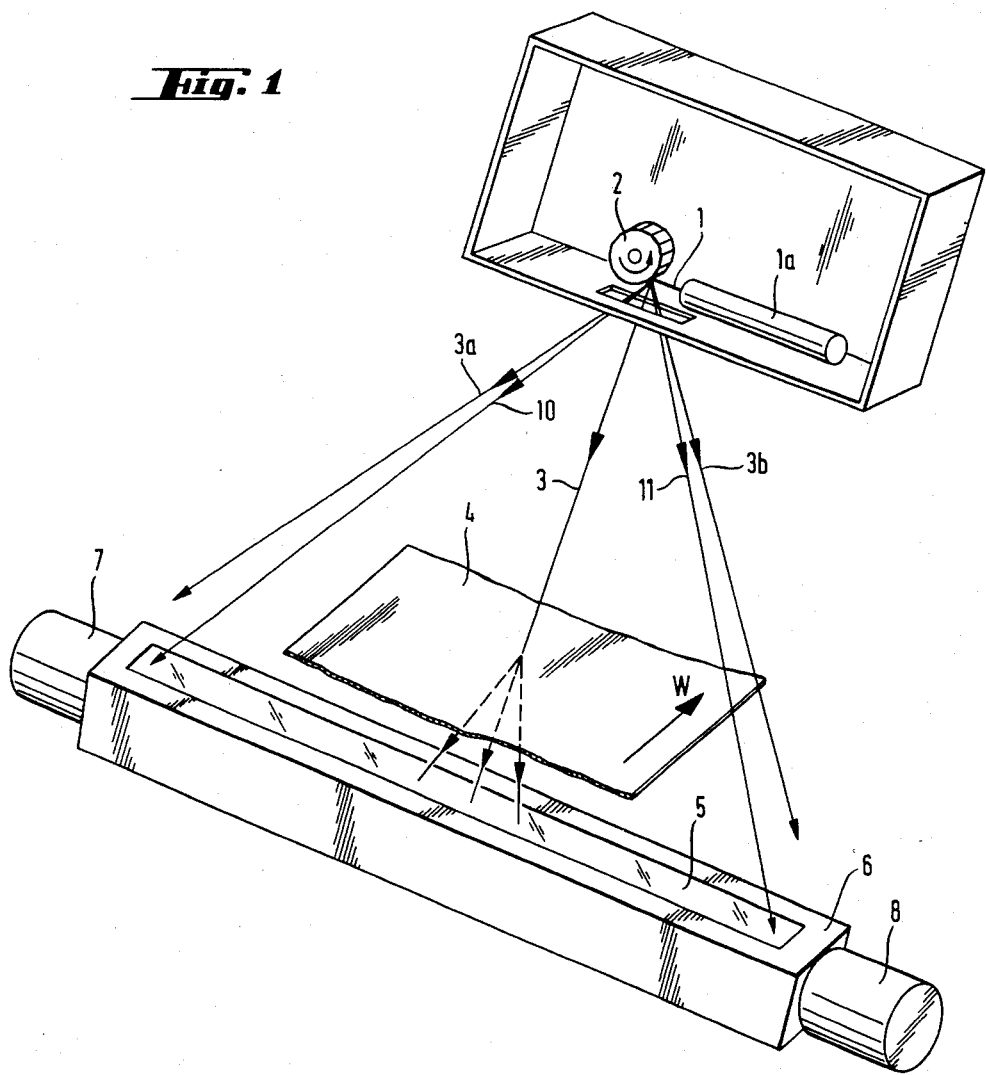

United States Patent [19]

Ikin

[11] Patent Number: 4,522,497

[45] Date of Patent: Jun. 11, 1985

[54] WEB SCANNING APPARATUS

[75] Inventor: John B. Ikin, Leigh-on-Sea, England

[73] Assignee: Ciba Geigy AG, Basel, Switzerland

[21] Appl. No.: 385,593

[22] Filed: Jun. 7, 1982

[30] Foreign Application Priority Data

Jun. 17, 1981 [GB] United Kingdom ................ 8118575
Jun. 17, 1981 [GB] United Kingdom ................ 8118576
Sep. 30, 1981 [GB] United Kingdom ................ 8129538
Nov. 27, 1981 [GB] United Kingdom ................ 8135928

[51] Int. Cl.$^3$ ............................................. G01N 21/17
[52] U.S. Cl. .................................... 356/431; 356/243; 250/571
[58] Field of Search ............... 356/445, 243, 429, 431; 250/571

[56] References Cited

U.S. PATENT DOCUMENTS 3,803,474  4/1974  Clarke ................................ 318/640
3,826,578  7/1974  King et al. ........................... 356/237
3,843,890  10/1974 Anthony et al. ..................... 250/563
4,108,533  8/1978  Sick et al. ........................... 350/6.7
4,422,766  12/1983 Skukalek ............................ 356/429

FOREIGN PATENT DOCUMENTS 1125679  3/1962  Fed. Rep. of Germany .
1296822  6/1969  Fed. Rep. of Germany .
1573900  4/1970  Fed. Rep. of Germany .
1573641  4/1970  Fed. Rep. of Germany .
2043876  3/1972  Fed. Rep. of Germany .
2018985  10/1979 United Kingdom .

Primary Examiner—R. A. Rosenberger
Attorney, Agent, or Firm—Harry Falber

[57] ABSTRACT

A method and apparatus of photoelectrically scanning a moving web material is described which comprises scanning the web with a narrow light beam sweeping across and beyond the edges of the web, directing light reflected or transmitted by the web to a light receiver of a light measuring unit so generating a corresponding electrical signal, and optically or electronically simulating the optical reflexion or transmission property of the web for two auxiliary scanning zones adjacent the lateral edges of the web in such manner that the average strength of said electrical signal remains constant over substantially the whole scanning sweep.

By use of this method abrupt changes in electronic signals received by the receiver when the scanning beam traverses the edges of the web are minimized. The effect of flare is also reduced.

32 Claims, 25 Drawing Figures

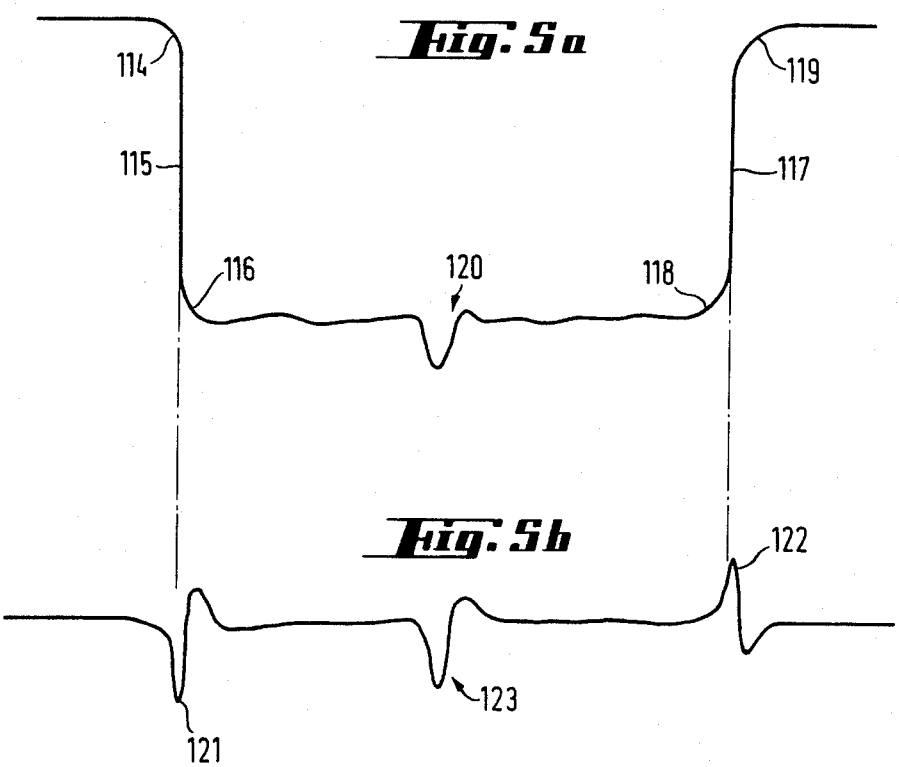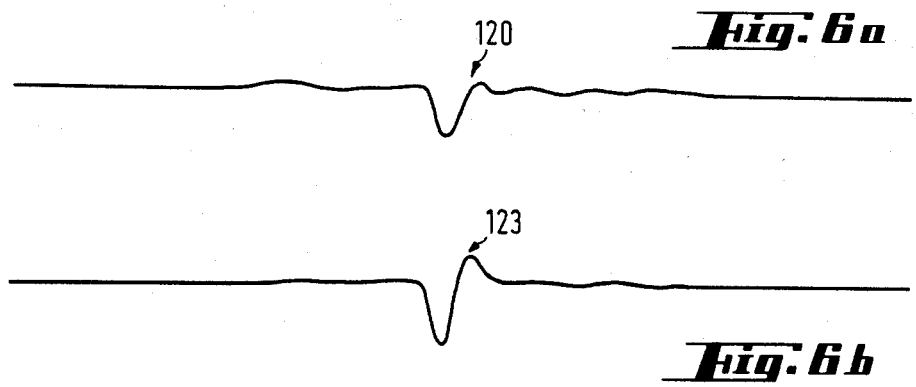

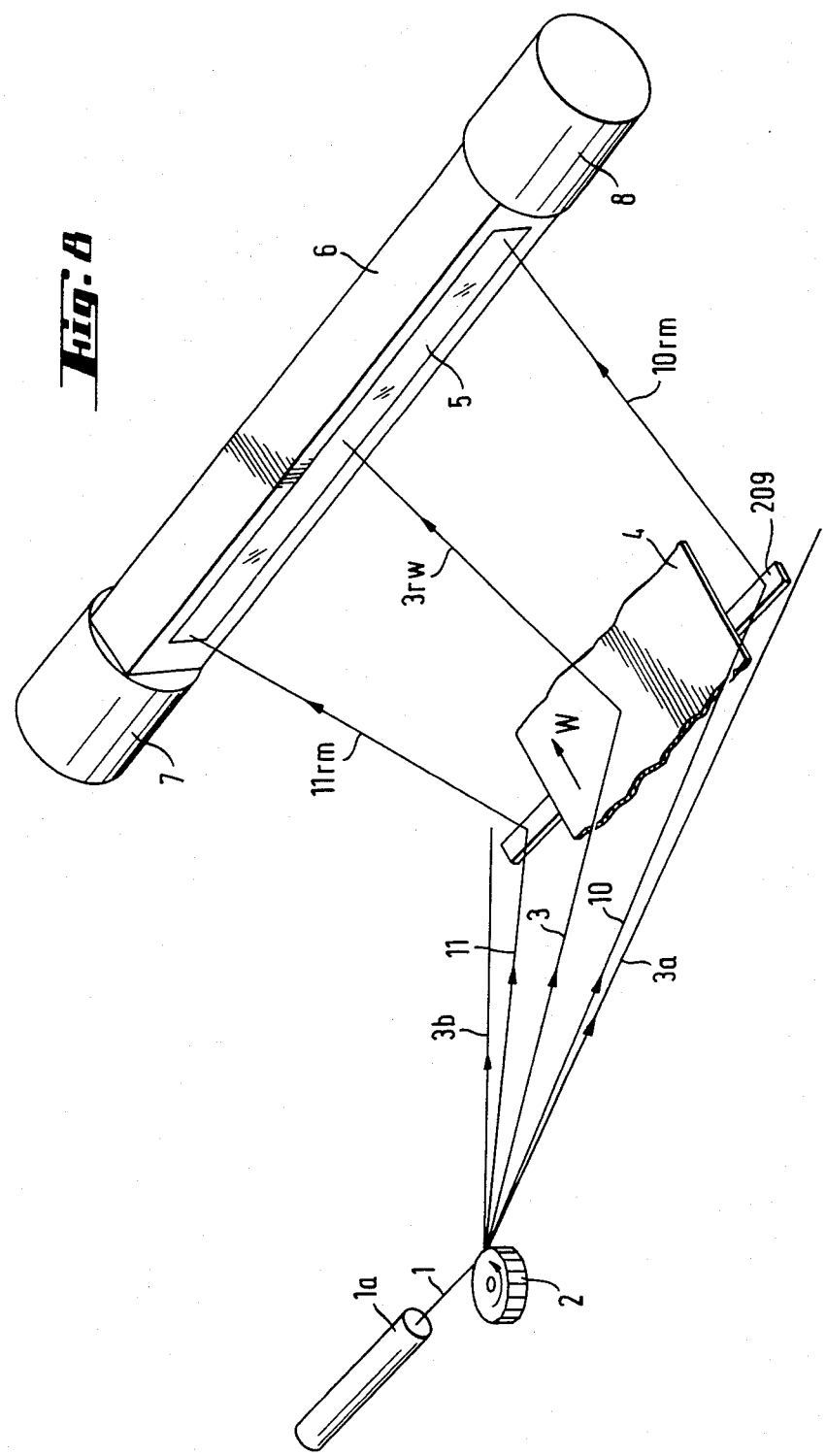

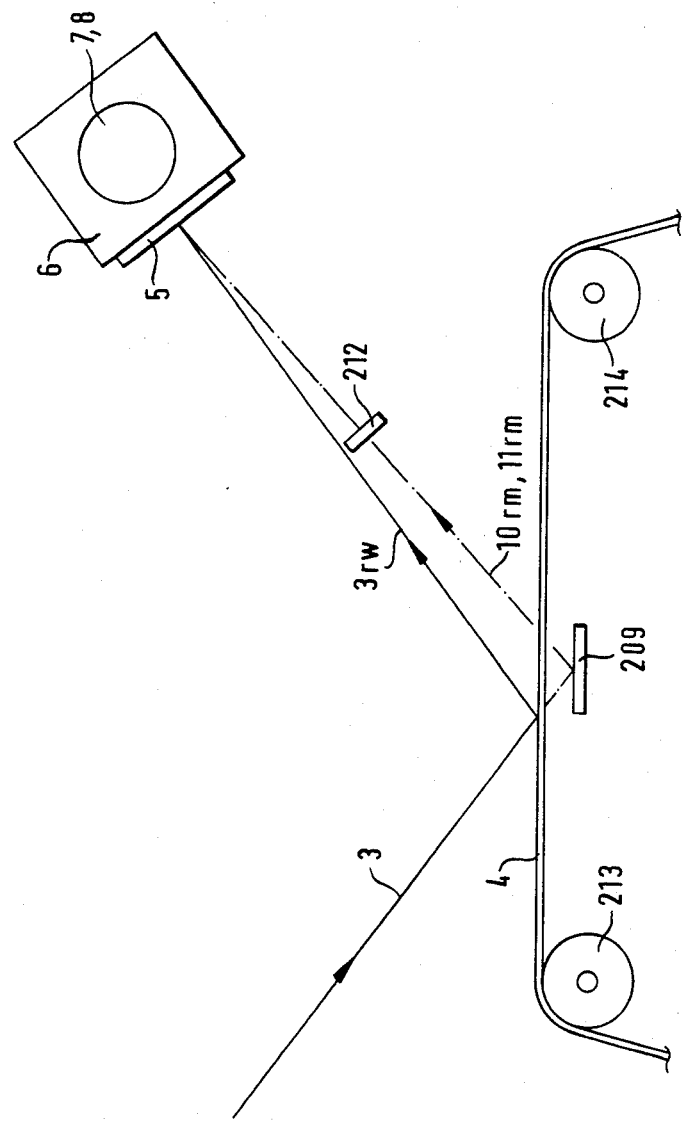

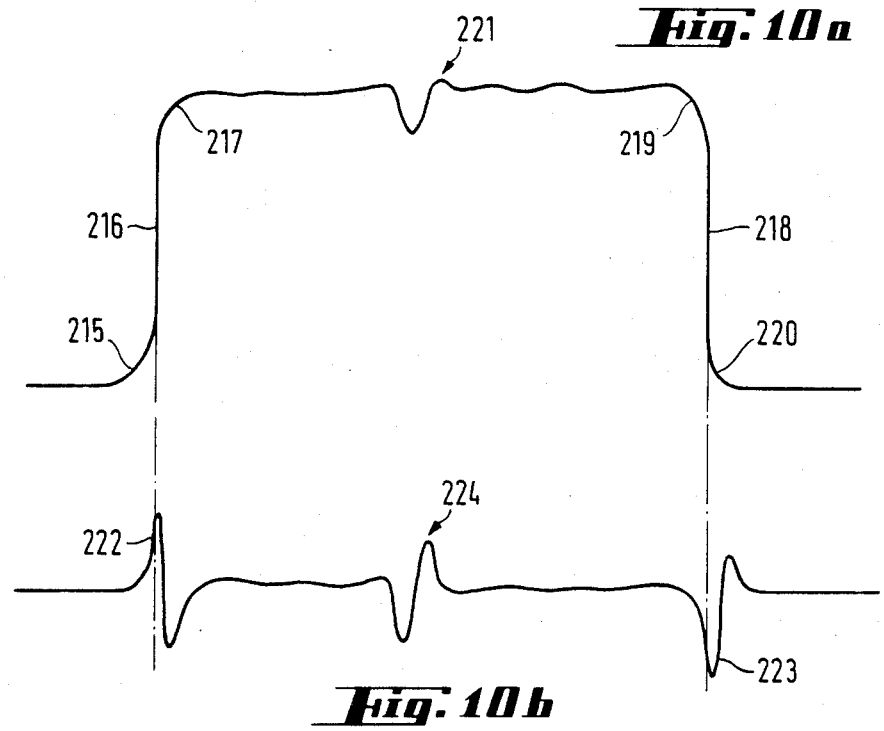
Fig. 10a
Fig. 10b
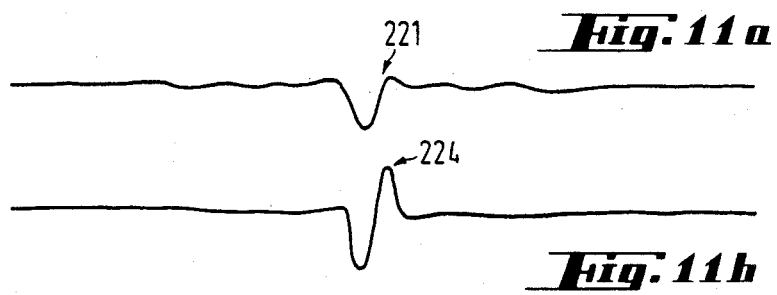
Fig. 11a
Fig. 11b

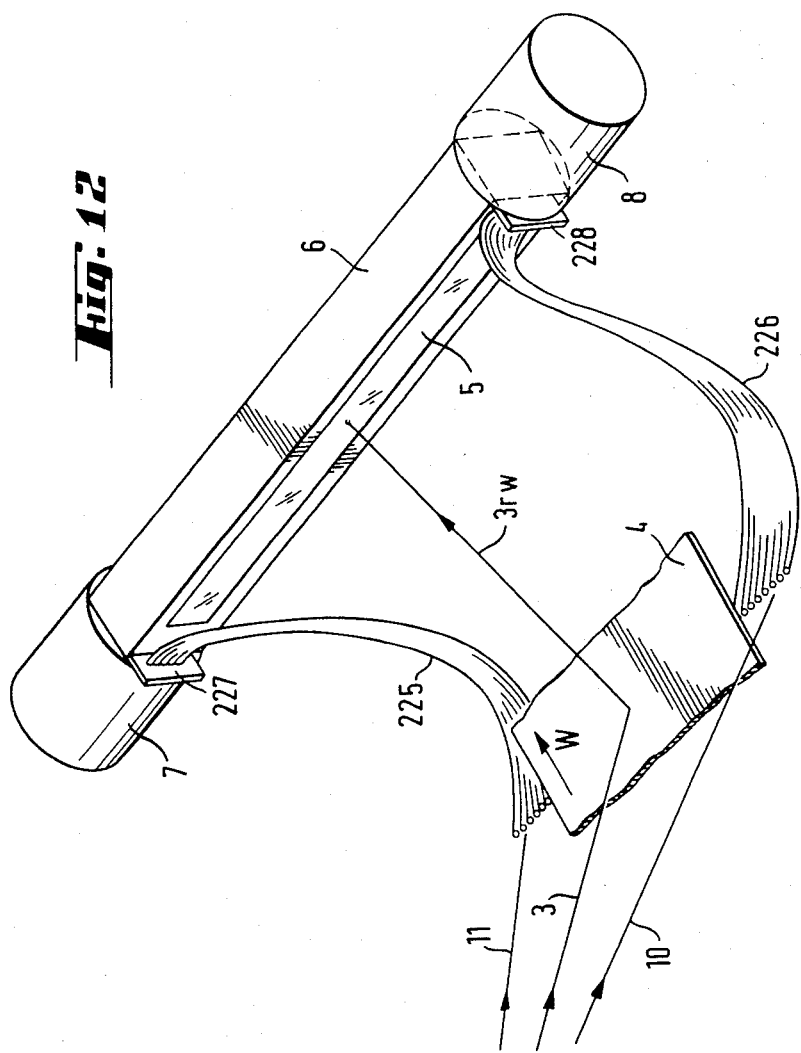

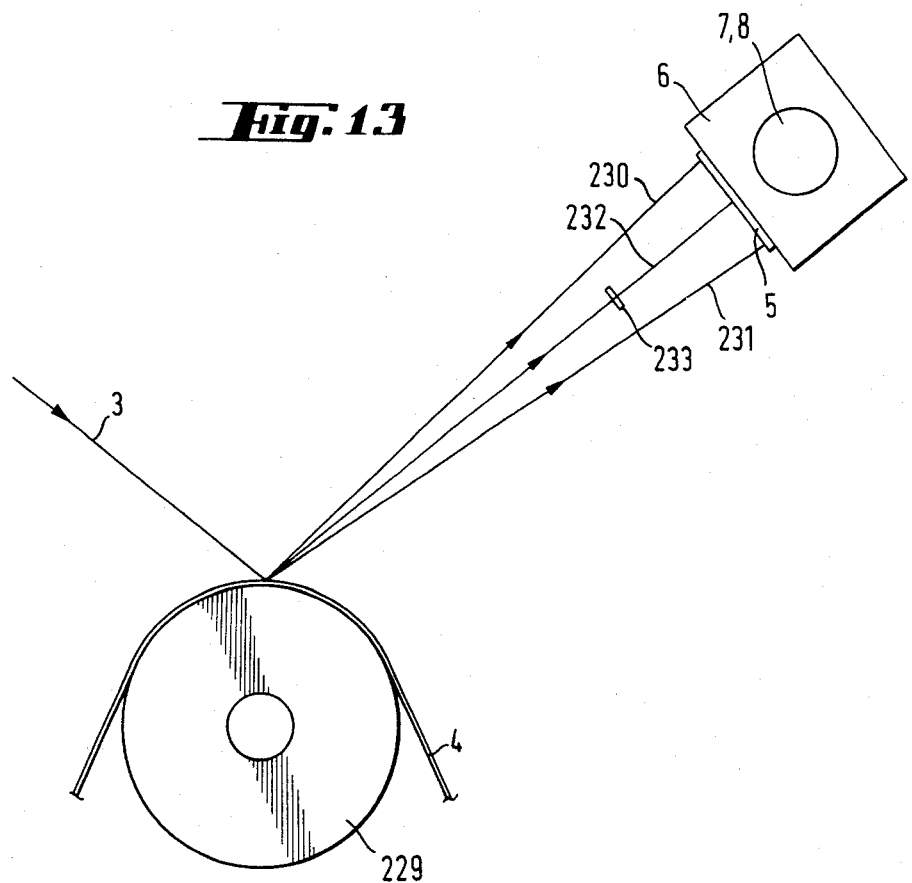

WEB SCANNING APPARATUS

This invention relates to a method of inspecting web material by scanning with a very narrow beam of light—typically a laser beam. In the conventional method, the beam is scanned across the web by an oscillating reflector or a multi-faceted mirror drum to be reflected by or transmitted by the web. The light subsequently enters a receiver system which converts the optical energy into an electronic signal.

This method has a drawback in that the resultant signal necessarily abruptly changes as the beam traverses the edges of the web and this change excites a transient in the signal processing circuitry. To ensure against the consequent tendency for a spurious alarm signal it is usually necessary to switch out or modify the response of the system for a short interval after the edge has been traversed. In addition, a further problem arises from any flare light often present in the immediate vicinity of the beam axis, for example through scatter from a slightly tarnished reflecting surface. The presence of flare necessarily rounds off the shoulders of the waveform at the instances of traverse of the two edges of the web. This can also tend towards a spurious alarm signal. These effects tend to render the system incapable of inspecting right to the extreme edges of the web and the non-examined strips may be several millimeters wide. This may be intolerable for some products, for example when pre-slit webs of photosensitive material are being examined for faults.

It is the object of the invention to reduce the width of non-examined strips of web material being scanned.

Accordng to the present invetion there is provided a method of photoelectrically scanning a moving web material which comprises scanning the web with a narrow light beam sweeping across and beyond the edges of the web, directing light reflected or transmitted by the web to a light receiver of a light measuring unit so generating a corresponding electrical signal, and optically or electronically simulating the optical reflexion or transmission property of the web for two auxiliary scanning zones adjacent the lateral edges of the web in such manner that the average strength of said electrical signal remains constant over substantially the whole scanning sweep.

Preferably in the method of the present invention the light reflected or transmitted by the web and the light passing the web within the auxiliary scanning zones is directed to a common light receiver, and a light modulating, i.e. attenuating, element is present in the optical path of said light passing the web; said light modulating element simulating the reflexion or transmission property of the web.

The term light in this context includes not only visible light but also infra-red and ultraviolet light. The method of the present invention is of particular use in the scanning of light-sensitive photographic web material. Such web material often comprises coated on a transparent plastics base a photosensitive layer which is light-transparent but also light scattering. Thus light which passes through such material is also diffused or scattered. Such photographic material must be examined for coating faults using scanning beams of non-actinic light, usually infra-red light is used.

The coating on photographic film material also partially reflects light. Furthermore if the web material is paper based the web wholly reflects the scanning light. Thus the signals obtained by scanning photographic web material may be detected, depending on the circumstances, either by reflection or transmission.

In the method of the present invention preferably a laser scanning beam is used. Preferably in the method of the present invention the beam is scanned across the web by use of an oscillating reflector or by use of a multifaceted mirror drum.

In one aspect of the method of the present invention use is made of the fact that the web is light transparent but also light scattering or diffusing.

Thus according to this aspect of the present invention there is provided a method of scanning light transparent diffusing web material which comprises scanning the web with a narrow light beam which is polarised, there being present between the web being scanned and a light receiver system a light transparent sheet of polarising material which protrudes beyond the edges of the web being scanned, the sheet of polarising material being oriented so as to partially extinguish the polarised scanning beam beyond the edges of the web.

In this aspect of the method of the present invention within the inspection zone, the polarised beam impinges on and is transmitted by the web. Due to the diffusing character of the web the transmitted light is no longer strongly polarised. A proportion of this light enters the receiver via the polarising sheet which further attenuates the intensity of the light. The degree of attenuation is not materially affected by the orientation of the sheet. At the scan extremities beyond the edges of the web the beam remains polarised as it has not passed through the web and is attenuated by the polarising sheet in accordance with the sheet orientation. Thus by orientation of polarisation of the source or orientation of the polarising sheet the signals resulting from transmission through the diffusing material may be closely matched to those corresponding to the scan extremities. However it may be supposed that the system is thereby rendered insensitive to defects in the web. Whereas this is true for major defects (for example large holes or absence of a diffusing layer on an otherwise transparent web) the presence of a subtle defect serves to modify the intensity of the transmitted light without causing a significant departure from randomness of polarisation. The system thus remains sensitive to such defects. It is usual practice to provide separate gross fault detectors which detect uncoated web and other major faults. Moreover, flare light is also predominantly polarised. It may be shown by a simple analysis that signal transients at the instance of traversing the edges of the web are almost entirely eliminated by adoption of the method of the present invention. In a practical system based on this method it has been possible to reduce the non-examined edge strips to 0.5 mm in width.

In another aspect of the method of the present invention use is made of the reflection properties of the moving web.

Thus according to this aspect of the present invention there is provided a method of scanning light reflecting web material which comprises scanning the web with a narrow light beam and directing a proportion of the light reflected from the web surface to a light receiver, there being present on the side of the web remote from the light source light redirecting means which is so positioned that a portion of the light which traverses the edges of the web is redirected to the same light receiver which receives light reflected from the web, there being present either in the path of the light reflected from the web or in the path of the light redirected to the receiver from the light redirecting means a light attenuating filter of such strength that the average strength of the electrical signal produced by the receiver due to the light reflected from the web is equal to the average strength of the electrical signal due to the light redirected to the receiver from the light redirecting means.

Usually the intensity of the light redirected by the light redirecting means will be greater than the intensity of the light reflected from the web and thus the light attenuating filter will be placed in the path of the redirected light.

Hereinafter the method of the present invention will be described with the light attenuating filter means present in the path of the redirected light.

The light attenuating filter used may be of the graded density type. Another useful light attenuating filter which may be used in the method of the present invention comprises two superimposed light polarising sheets, one oriented with respect to the other to attenuate the light.

Preferably the light redirection means is a reflection means.

When light reflection means is used to redirect light the web may be unsupported at the point of scanning and a light reflecting strip is placed so as to protrude beyond either edge of the web on the side of the web remote from the light scanning source at the point of scanning. Thus the light is redirected to the receiver by reflection.

Preferably the light reflecting means is a mirror.

Alternatively the scanning beam may be polarised light and the light reflecting means beyond the edges of the web may be a polarising sheet so oriented to attenuate the light reflected therefrom.

Alternatively the web supporting means at the point of scanning is a polished roller which also redirects light to the receiver by reflection.

However the light redirecting means may be light conduction means for example an array of light pipes. In another aspect of the present invention light refraction means is used to redirect light which traverses the edges of the web to the receiver.

Depending on whether the web is specularly reflecting or diffusively reflecting it is possible to alter the nature of the redirecting means to achieve a signal matching that of the reflected light from the web and then by use of the light attenuating filter it is possible to eliminate almost entirely signal transients at the instance of traversing the edges of the web during the web scanning. In a practical system based on one of these techniques the non-examined strips have been reduced to 0.5 mm in width.

In the method of the present invention preferably a laser scanning beam is used.

According to yet another aspect of the method of the present invention light reflected or transmitted by the web is directed to a first light receiver and the light passing the web within the auxiliary scanning zones is directed to a second light receiver, and wherein the output signals of the light receivers are so matched and added that the resulting sum signal remains constant over substantially the whole scanning sweep.

This particular method is of most use when the light is reflected from the web.

In some cases it is required to know when the light scanning beam traverses an edge of the web thus in such cases it becomes necessary to generate an electronic signal corresponding to the traversing of the beam across the edge of the web for the purpose of, for example, electronic selection of signals only appropriate to the inspection of the web itself or tracking of linear defects.

Thus in the method wherein the light is transmitted through the web by insertion of the polarising sheet as prior described the edge of the web has been rendered transparent to the light gathering receiver. It is possible to divert a proportion of the light entering the polarising sheet towards the window of an auxiliary photodetector. This diverted light may be a fixed proportion of the incident beam intensity when not impinging on the web or the same fixed proportion of the light scattered by the web. The consequent electronic signal will thus abruptly change at the instant of traversing the edge of the web by the scanning beam. This abrupt change can be used for electronic switching. To divert such a proportion of the light a beam splitting device may be inserted between the web and polarising sheet or the reflecting surface of the polarising sheet may be used itself as a beam splitter.

Similarly in the method wherein the light is reflected from the web by the matching process defined above the edge of the web has been rendered transparent to the light gathering receiver. It is consequently necessary to direct a proportion of the light entering the light attenuating filter towards the window of an auxiliary photodetector. The resulting radiation is a fixed proportion of the incident beam intensity when not impinging on the web or the same fixed proportion of the light attenuating by transmission through the web prior to entering the filter. The consequent electronic signal will thus abruptly change at the instant of traversing the edge of the web by the scanning beam. This abrupt change can be used for electronic switching as already described. To divert such a proportion of the light a beam splitting device can be inserted into the path immediately in front of the light attenuating filter.

According to another aspect of the present invention there is provided a scanning apparatus for a moving web comprising means for generating a narrow scanning light beam and sweeping the beam across and beyond the edges of the web, a measuring unit including a light receiver generating an electrical output signal corresponding to the light received, means for directing the light reflected or transmitted by the web to said light receiver, optical or electronical means for simulating the optical reflection or transmission property of the web for two auxiliary scanning zones adjacent the lateral edges of the web in such manner that the average strength of sad electrical output signal remains constant over substantially the whole scanning sweep.

Preferably in this apparatus the light directing means direct the light reflected or transmitted by the web as well as the light passing the web within said auxiliary scanning zones to said light receiver, and wherein the simulating means is an optical light modulating element present in the optical path of the light passing the web.

In one preferred apparatus the light modulating element consists of two light polarising sheets mutually oriented to obtan a degree of attenuation.

When the apparatus acts by scanning the web material and receiving signals transmitted by the web preferably the light scanning means is a source of polarised light and the light modulating element is a polarising sheet.

Preferably the polarising sheet is arranged in the direction of the scanning light behind the web and extends across the web and the auxiliary scanning zones.

When the apparatus acts by scanning the web material and receiving signals reflected from the web preferably the light modulating element is an optical density wedge.

In this apparatus preferably the light reflecting surfaces are constructed by a mirror extending across the web. In another embodiment the reflecting surfaces are constituted by the reflecting surface of a polished roller supporting the web at the point of scan.

In one embodiment of the apparatus the light directing means comprises light conducting means conducting light passing the web to the light receiver.

In another embodiment of the apparatus according to the present invention the measuring unit comprises two light receivers with associated amplifiers and an adder for the output signals of the amplifiers, the light directing means directing light reflected or transmitted by the web to one light receiver and light passing the web within the auxiliary scanning zones to the other light receiver, and the amplifiers being mutually matched so that the sum signal generated by the adder remains constant over substantially the whole scanning sweep.

Preferably in the apparatus of the present invention there is provided a web edge detector which comprises an additional light receiver arranged to receive light both from the web and one auxiliary scanning zone.

In the apparatus of the present invention preferably the light source used to generate the light beam is a laser. Preferably an oscillating reflector or multi-faceted mirror is used in the apparatus to cause the beam to scan across the web.

The accompanying drawings will serve to illustrate the invention.

FIGS. 1 to 3 and 5a to 7c relate to an apparatus and method wherein light is transmitted through the web.

FIGS. 8 to 16b relate to an apparatus and method wherein light is reflected from the web.

Figure 4A:
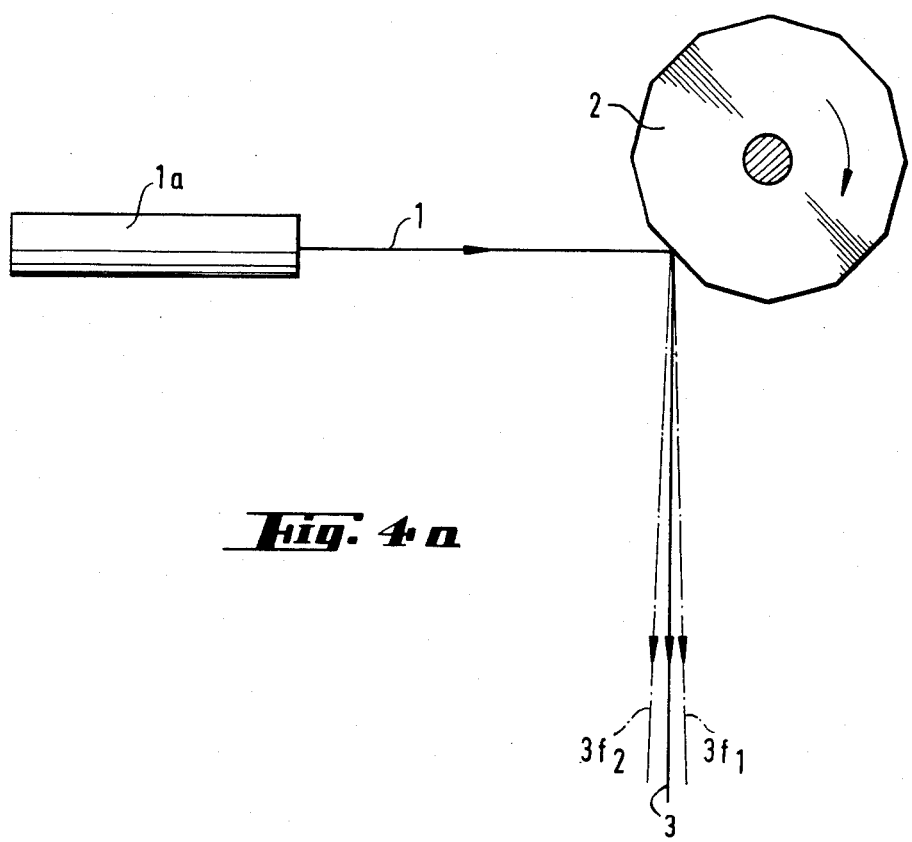
Figure 4B:
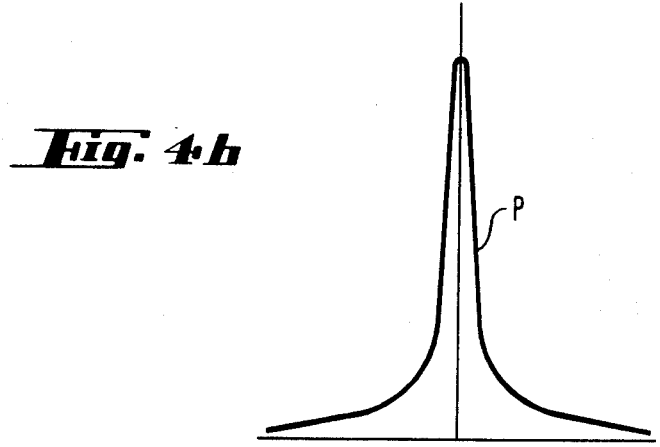

FIGS. 4a and 4b related to both reflection and transmission methods.

In all the figures the same numbers have the same signification.

FIG. 1 shows a typical system by which a web is inspected according to the prior art by light transmission. A laser beam 1 from a laser source 1a is projected onto a rotating faceted mirror drum 2 from which a reflected beam 3 is scanned over a path bounded by 3a and 3b thereby to impinge on the web 4. The impingement point traverses the web in a direction normal to the direction W of the motion of the web. The beam 3 is modified and partially transmitted by the web 4 to fall on the window 5 of the receiver 6 containing photocells 7 and 8. Also shown are paths 10 and 11 taken by the beam during that part of the scan when the beam does not impinge on the web but falls directly on the window 5 of the receiver 6.

Figure 2:
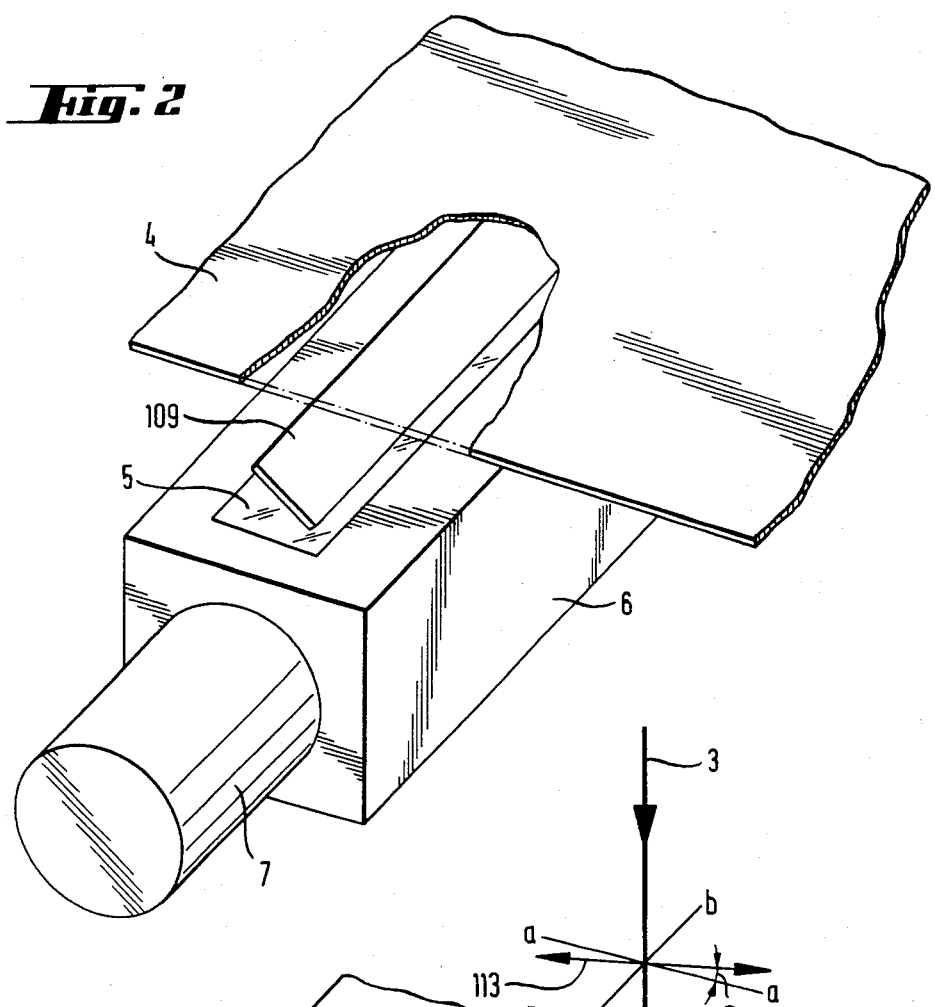

FIG. 2 shows how in the same configuration of apparatus as shown in FIG. 1 a polarising strip 109 is interposed between web 4 and the hole of window 5 of receiver 6. The plane of the polarising strip 109 is inclined relative to the plane of the scan as shown.

Figure 3:
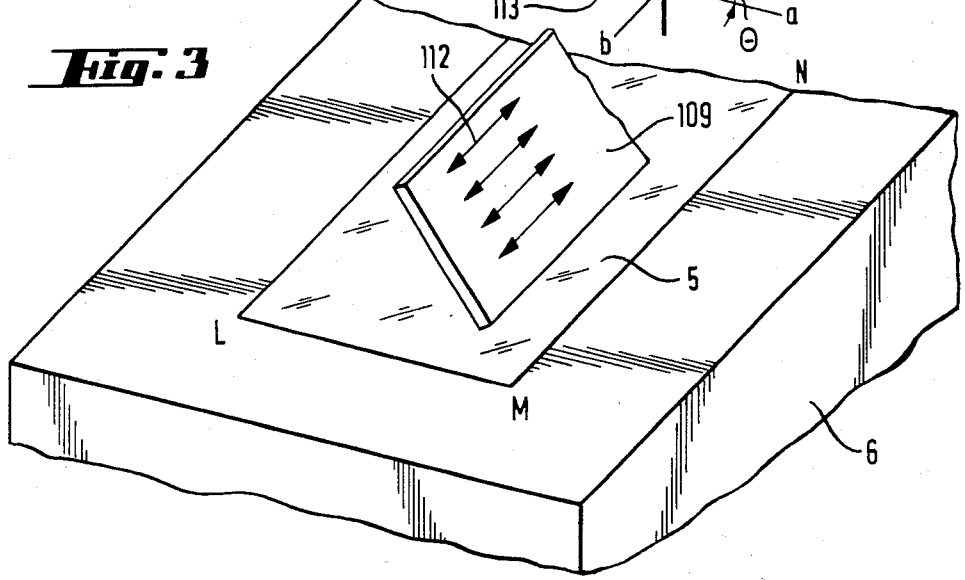

FIG. 3 shows in the strip 109 of FIG. 2 preferred direction 112 of polarisation of the strip 109. Thus light beam 1 and therefore light beam 3 is polarised. The beam in this figure is shown in the position normal to window 5 in the absence of web 4. The direction 113 of polarision of beam 3 is chosen to be at small angle $\theta$ relative to axes aa and bb drawn parallel to edges LM and MN of window 5 respectively.

FIGS. 4a–b show the effect of a slightly tarnished mirror drum surface.

FIG. 4a shows how the beam 1 from the laser source is reflected by a slightly tarnished mirror surface on the faceted drum 2 to form the main beam 3 together with a narrow cone of beams typically bounded by rays $3f_1$ and $3f_2$ axisymmetrically situated about the main beam. This cone of beams is referred to as flare light.

FIG. 4b shows the profile P of the main beam and associated flare light.

FIGS. 5a–b show how the prior art system is rendered incapable of inspecting strips at the edges.

FIG. 5a shows how the combined unfiltered signal from photocells 7 and 8 changes as the beam 3 is scanned between extreme paths 3a and 3b.

Immediately prior to main beam 3 falling on the web a portion $3f_1$ impinges on the web 4 to be partially attenuated by the web 4 before entering the receiver 6 via window 5. The signal strength thus commences to fall as at 114. As the scan proceeds to allow the main beam 3 to fall on the web the signal rapidly falls as at 15. Thereafter a portion of the flare light is additionally attenuated to produce the slow fall as at 116. Similar abrupt change 117 and rounding effects 118 and 119 occurs in reverse as the trailing edge is traversed by the scanned beam. The response to a typical defect in the web or its coating is shown as 120 in FIG. 5a.

FIG. 5b shows the signal after appropriate high-pass filtering. Transients 121 and 122 due to abrupt changes 115 and 117 respectively together with effects 114, 116, 118 and 119 are seen to be similar in magnitude to the transient 123 generated by the defect and are therefore not distinguishable without appropriate signal gating and consequent loss of inspection near the edges.

FIGS. 6a–b show how according to the present invention relating to inspection by transmission through the web that it is possible to inspect the web over its entire surface.

FIG. 6a shows how both the polarising strip 109 together with correct polarisation of the beam 3 influences the signal together as the beam 3 is scanned between extreme paths 3a and 3b.

The main beam is polarised and the associated flare light is also predominatly polarised and the associated flare light is also predominatly polarised along the same plane. At any stage immediately prior to or after transfer of the beam 3 across an edge of the web any elementary beam whether main beam 3 or a beam within the cone of flare light is either transmitted through the polarising strip 109 and attenuated according to the value of $\theta$ or is partially transmitted by the web by which it is rendered randomly polarised and subsequently attenuated at strip 109 by an amount independent of $\theta$. It is possible to select a value of $\theta$ such that the signal resulting from any such elementary beam is substantially the same whether impinging on the web or not. The resultant combined signal is thus essentially free of transients at the instant of traverse of the beam across the edges of the web. The only remaining transient 120 is that generated by a real defect. It is thus now possible to inspect the web 4 over its entire surface.

FIG. 6b shows the signal 123 after appropriate filtering to segregate abrupt changes from slow changes.

Figure 7A:
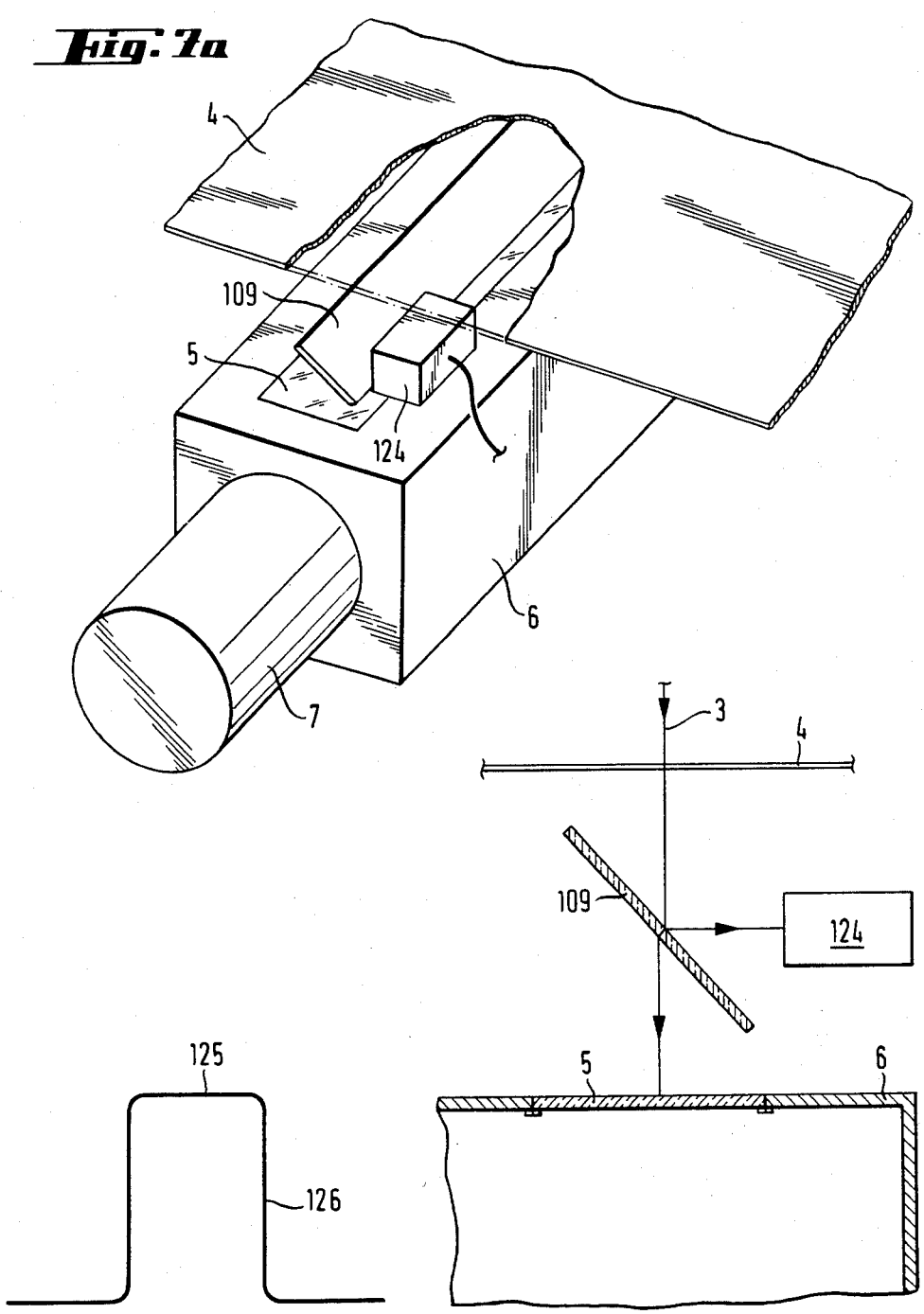
Figure 7C:
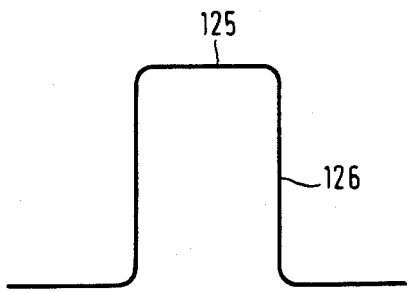
Figure 7B:
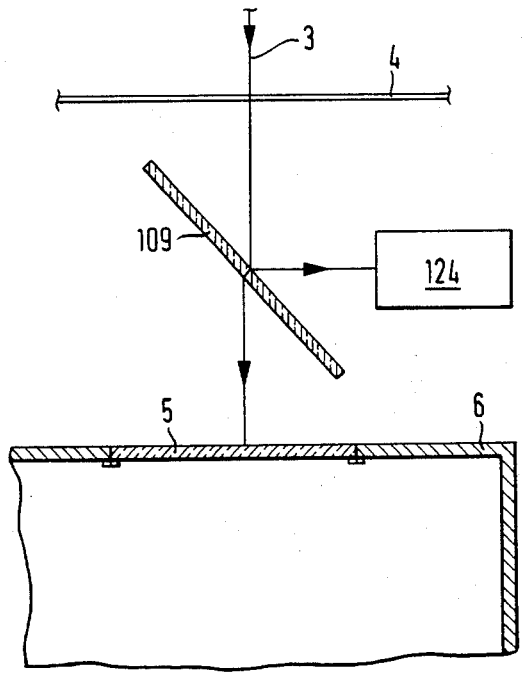

FIGS. 7a–c show how the system can be adapted to provide a web edge detector.

FIG. 7a shows how by appropriate choice of the angle of inclination of polarising strip 109 a proportion of light transmitted past the edge of the web 4 or scattered by the web in the vicinity of the edge may be reflected by the surface of the polarised strip 109 towards a second light receiver or detector 124. The residual light is transmitted through the polarised strip 109 in the manner already described.

FIG. 7b shows the same configuration seen in side elevation.

FIG. 7c shows the response 125 generated by auxiliary photocell 124 as an edge is traversed. Abrupt change 126 may be used for electronic switching purposes.

FIG. 8 shows a typical system by which the web is inspected by light reflection. A laser beam 1 is projected onto a rotating faceted mirror drum 2 from which the reflected beam 3 is scanned over a path bounded by 3a and 3b thereby to impinge on the web 4. The impingement point traverses the web in a direction normal to the direction W of the motion of the web. The beam 3 is modified and partially reflected by the web 4 as 3rw to fall on the window 5 of the receiver 6 containing photocells 7 and 8. The beam 3 is caused to scan beyond the edges of the web and thence fall on a reflecting strip 209. Light rays 10 and 11 indicate such typical beams. These beams are reflected along directions 10rm and 11rm respectively to enter the same window 5 of the receiver 6.

FIG. 9 shows in side elevation how an attenuating filter 212 may be interposed in the redirected beams such as 10rm and 11rm. The filtrate density is such that the average strength of the electrical signal produced by the photocells 7 and 8 due to light reflected by the web 4 is equal to the average strength of the electrical signal due to the light redirected to the receiver from the mirror 209 via the filter 212. In this figure the web is supported by two rollers 213 and 214.

Reference is again made to FIGS. 4a-b which show the effect of a slightly tarnished mirror drum surface to produce a narrow cone of beams typically founded by rays $3r_1$ and $3f_2$.

FIGS. 10a-b show how without the filter 212 the system is rendered incapable of inspecting strips at the edges.

FIG. 10a shows how the combined unfiltered signal from photocells 7 and 8 changes as the beam 3 is scanned between extreme paths 3a and 3b.

Immediately prior to main beam 3 falling on the web a portion $3f_1$ impinges on the web 4 to be partially reflected by the web 4 to enter the receiver 6 via window 5. The signal strength thus commences to rise as at 215. As the scan proceeds to allow the main beam 3 to fall on the web the signal rapidly rises as at 216. Thereafter a portion of the flare light is additionally reflected to produce the slow rise at 217. Similar abrupt changes 218 and rounding effects 219 and 220 occur in reverse as the trailing edge is traversed by the scanned beam. The response to a typical defect in the web or its coating is shown as 221.

FIG. 10b shows the signal after appropriate high-pass filtering. Transients 222 and 223 due to abrupt changes 216 and 218 respectively together with effects 215, 217, 219 and 220 are seen to be similar in magnitude to the transient 224 generated by the defect are therefore not distinguishable without appropriate signal gating and consequent loss of inspection near the edges.

FIGS. 11a-b show how according to the present invention relating to inspection by reflection from the web that it is possible to insplect the web over its entire surface.

FIGS. 11a show how the combined unprocessed signal from photocells 7 and 8 changes as the beam 3 is scanned between extreme paths 3a and 3b.

At any stage immediately prior to or after transfer of the beam 3 across an edge of the web any elementary beam whether main beam 3 or a beam within the cone of flare light is either reflected by the web to enter the receiver and thus photocells 7 and 8 or is redirected by mirror 209 via filter 212 to the same photocells. The signal resulting from any such elementary beam is thus substantially the same whether impinging on the web or not. The resultant combined signal is thus essentially free of transients at the instant of traverse of the beam across the edges of the web. The only remaining transient 221 is that generated by a real defect. It is thus now possible to inspect the web 4 over its entire surface.

FIG. 11b shows the signal after appropriate high-pass filtering to segregate abrupt changes from slow changes.

FIG. 12 shows an alternative embodiment. Two light pipe arrays 225 and 226 are used in place of reflecting strip 209 to redirect light to photocells 7 and 8 via filters 227 and 228 respectively. If the signal strength due to reflection from the web 4 exceeds that due to transmission through the light pipe arrays 225 and 226 a filter is instead placed across the window 5 of the light receiver 6.

FIG. 13 shows how yet another alternative embodiment of the invention the web may be suported at the line of scan by a highly polished roller 229. The light reflected by the web is often scattered over a finite range of directions typically bounded by planes 230 and 231. The light is specularly reflected by the polished roller 229 at the scan extremities typically along plane 232. Matching of the average signal strengths due to the web and roller may be achieved by placing a thin strip of filter material 233 of appropriate optical density in the plane 232.

Figure 14A:
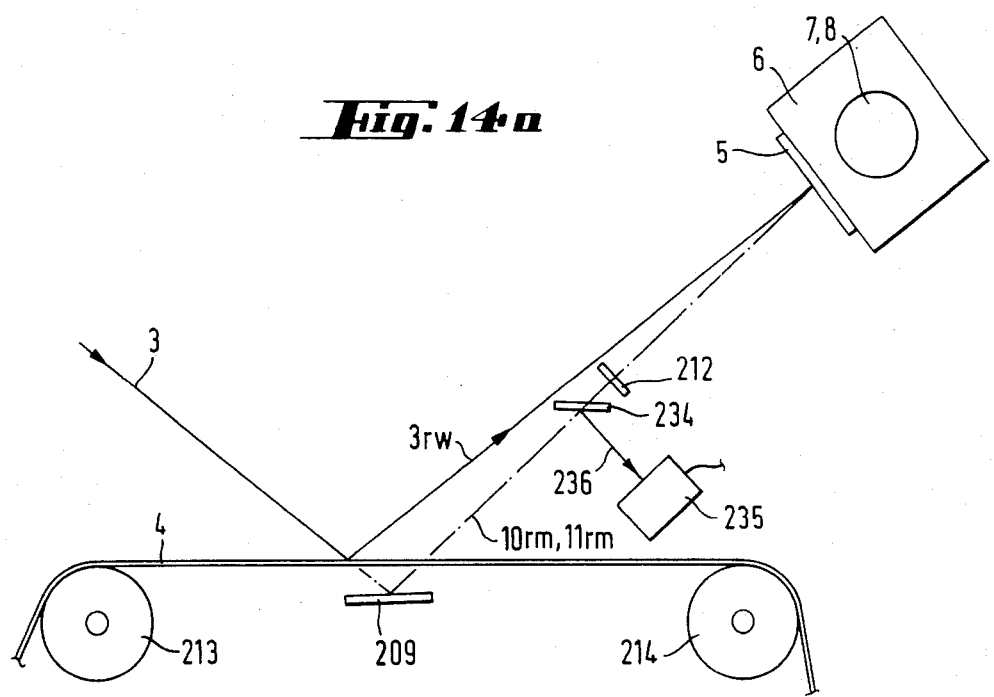
Figure 14B:
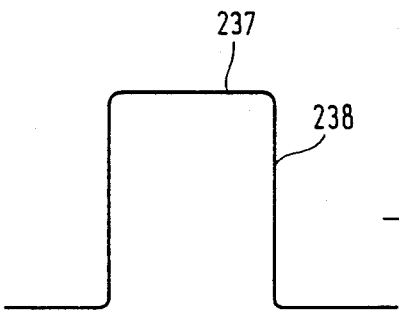

FIGS. 14a-b show how the system illustrated in FIG. 9 may be adapted to provide a web edge detector.

In FIG. 14a a beam splitter 234 is inserted into the plane light path formed by redirected beams such as 10rm and 11rm. This beam splitter directs a proportion of the redirected light to fall on an auxiliary photocell 235 as shown by ray 236.

FIG. 14b shows the response 237 generated by auxiliary photocell 235 as an edge if traversed by the beam 3. The abrupt change 238 may be used for electronic switching purposes.

Figure 15:
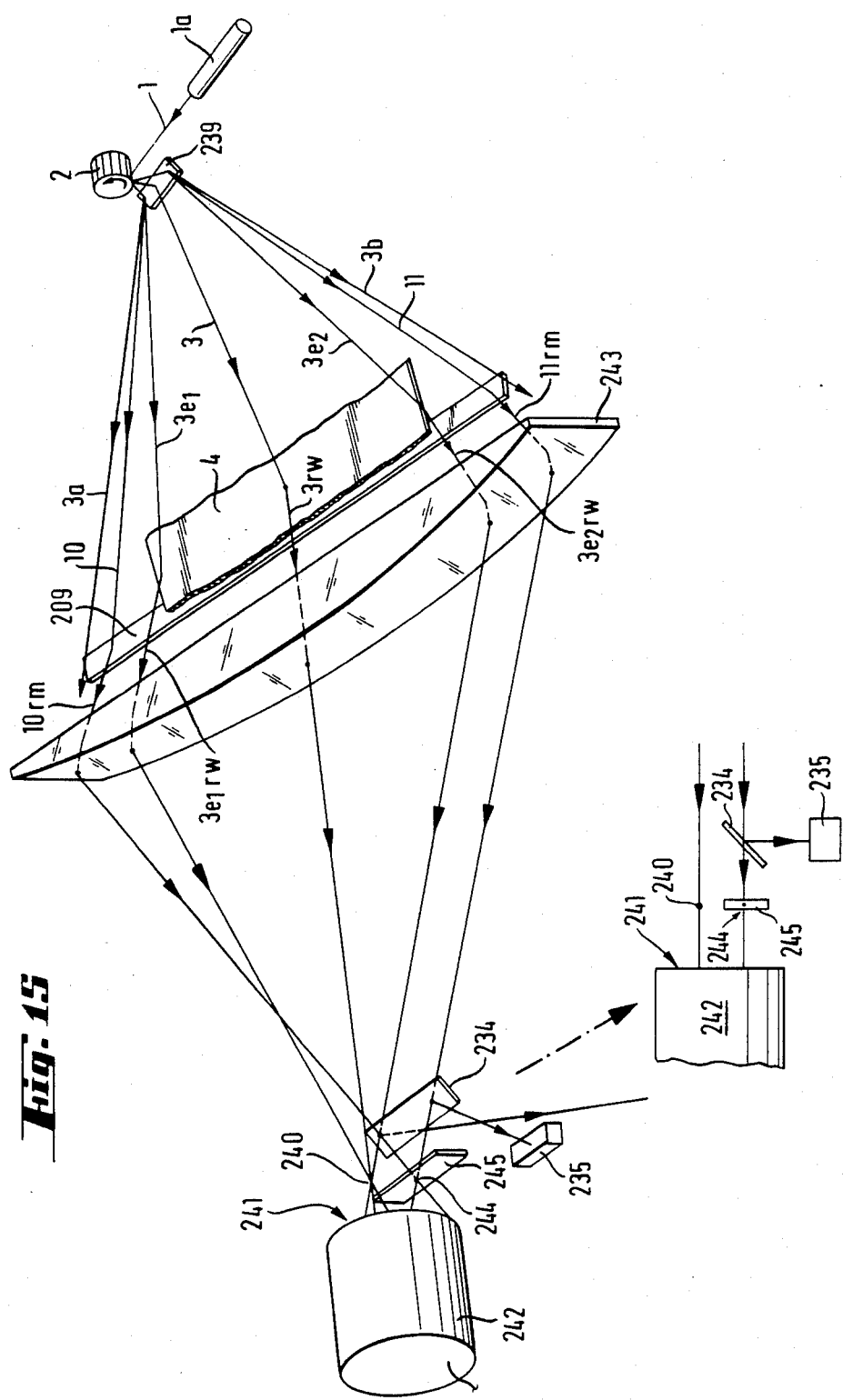

In FIG. 15 there is shown another embodiment wherein the light is focussed onto a photocell 242 by means of a lens.

Beam 1 from a laser source is projected onto a rotating faceted mirror drum 2 from which it is reflected and scanned after further reflection by mirror 239 over a path bounded by 3a and 3b thereby to impinge on web 4 and then beyond the edges of the web to fall on reflecting strip 209. The scanned beam 3 bounded by paths $3e_1$ and $3e_2$ is reflected by the web 4 to form a beam 3rw which scans between paths $3e_1rw$ and $3e_2rw$ and thence concentrated at point 240 in the vicinity of the window 241 of photocell 242 by the focussing curved lens 243 thereafter to fall on entrance window 241. The beams such as 10rm and 11rm reflected by mirror 209 are similarly concentrated at 244 by focussing lens 243 thereafter to fall on entrance window 241 of the photocell 242. Matching of signal strengths due to reflection by web 4 and by reflecting strip 209 is achieved by interposing a neutral wedge filter 245 at focus 244 but not so as to intercept beams focussed at point 240. Also shown is a beam-splitter 234 inserted into the path immediately in front of the neutral wedge 245 to direct a proportion of the light reflected by reflecting strip 209 towards the auxiliary photocell 235.

Thus in this embodiment it is arranged that the light reflected by the web 4 is focussed at one region of the receiving face of the photocell and similarly the light reflected by the mirror 209 is focussed at a different region of the same face. By placing a wedge filter 245 to cover this second focus but not the first it is possible to match the respective intensities corresponding to average reflection by the web and reflection by the mirror merely by adjusting the position of the wedge. Clearly this is advantageous if products with substantially different surface reflectivities are to be inspected.

Figure 16A:
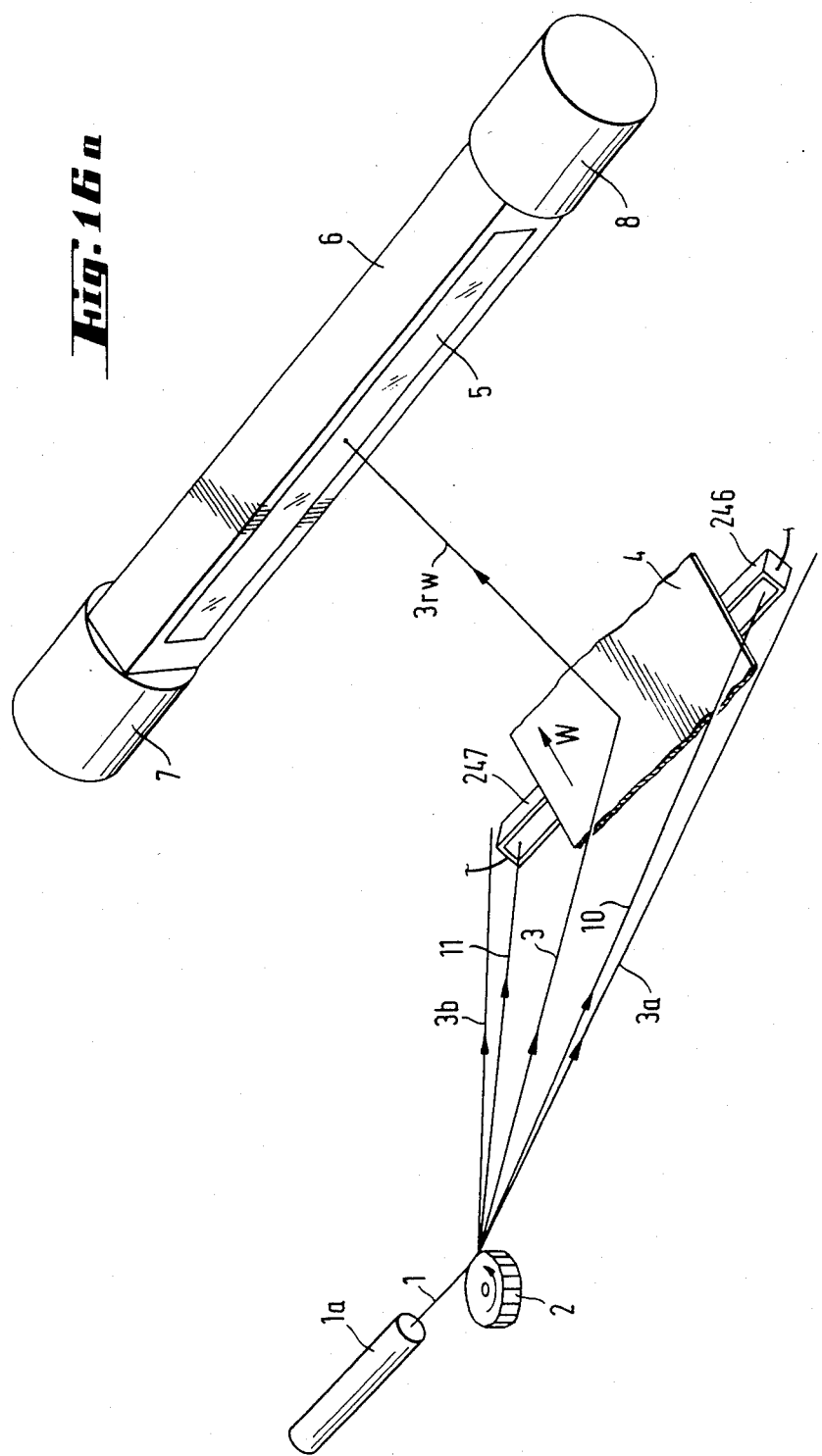
Figure 16B:
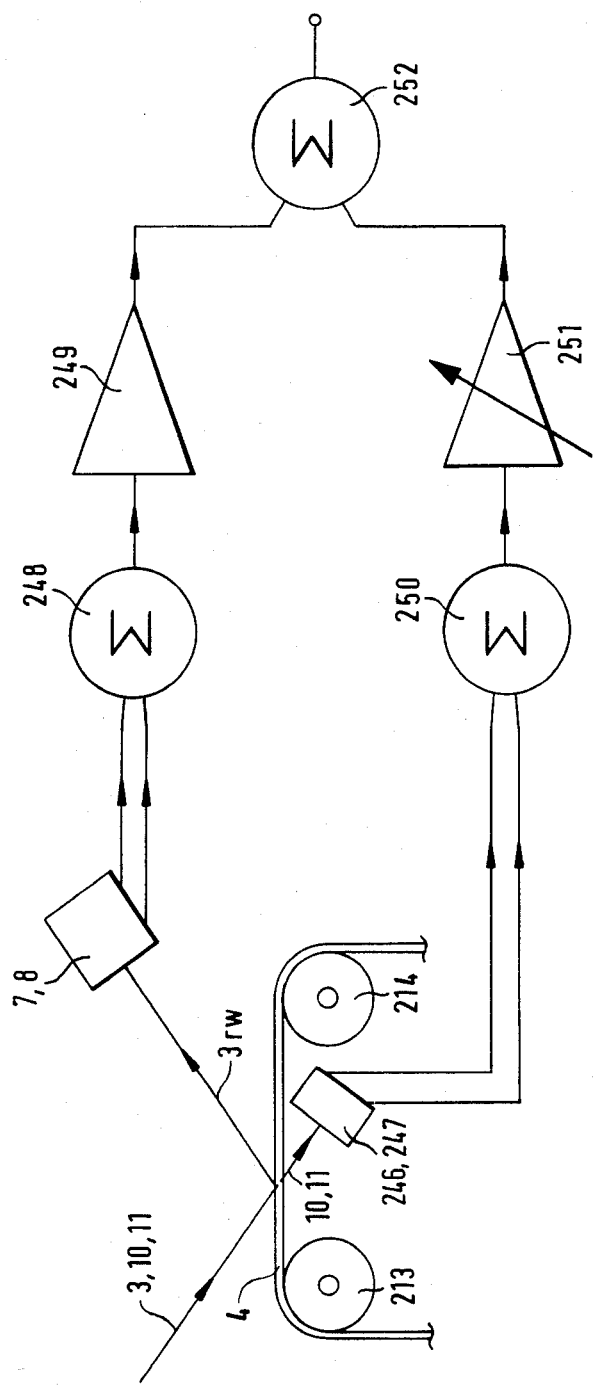

FIGS. 16a–b show how a combination of signals from a number of photocells may be used in yet another embodiment of the invention.

In FIG. 16a the beam 10 before traversing the leading edge of the web is allowed to fall on an auxiliary photocell 246. Similarly the beam 11 after traversing the trailing edge of the web is allowed to fall on a second auxiliary photocell 247.

FIG. 16b shows in schematic form how signals from photocells 7 and 8 due to light beams 3rw reflected by web 4 are added at a device 248 and amplified by amplifier 249. Similarly signals from auxiliary photocells 246 and 247 due to light beams 10 and 11 are added at a device 250 and amplified by variable gain amplifier 251. The gain of amplifier 251 is adjusted to equate its signal output to that of amplifier 249. Thus as any stage immediately prior to or after transfer of the beam 3 across the edge of the web any elementary beam whether main beam 3 or a beam within the cone of flare light is either reflected by the web any elementary beam whether main beam 3 or a beam within the cone of flare light is either reflected by the web either to enter the receiver and thus photocells 7 and 8 or to fall directly on photocells 246 or 247. The signal at the output of device 252 resulting from any such elementary beam is thus substantially the same whether reflected by the web or not and the only remaining transients in the consequent filtered signal are those generated by real defects. It is again possible to inspect web 4 over its entire surface.

The signal from amplifier 251 for example may be used for electronic signal switching purposes as already described.

I claim:

1. A method of photoelectrically scanning a moving web material which comprises scanning the web with a narrow light beam sweeping across and beyond the edges of the web, directing light reflected or transmitted by the web to a light receiver of a light measuring unit so generating a corresponding electrical signal, and optically simulating the optical reflexion or transmission property of the web for two auxiliary scanning zones adjacent the lateral edges of the web in such manner that the average strength of said electrical signal remains constant over substantially the whole scanning sweep.

2. A method according to claim 1 wherein the light reflected or transmitted by the web and the light passing the web within the auxiliary scanning zones is directed to a common light receiver, and a light attenuating element is present in the optical path of said light passing the web; said light attenuating element simulating the reflexion or transmission property of the web.

3. A method according to either claim 1 or claim 2 wherein a laser scanning beam is used.

4. A method according to claim 1, wherein the beam is scanned across the web by use of an oscillating reflector.

5. A method according to claim 1 wherein the web is of light transparent diffusing material which comprises scanning the web with a narrow light beam which is polarised, there being present between the web being scanned and the light receiver system a light transparent sheet of polarising material which protrudes beyond the edges of the web being scanned, the sheet of polarising material being oriented so as to partially extinguish the polarised scanning beam beyond the edges of the web.

6. A method according to any one of claim 1 wherein the web is of light reflecting material which comprises scanning the web with a narrow light beam and directing a proportion of the light reflected from the web surface to the light receiver, there being present on the side of the web remote from the light source light redirecting means which is so positioned that a proportion of the light which traverses the edges of the web is redirected to the same light receiver which receives light reflected from the web, there being present either in the path of the light reflected from the web or in the path of the light redirected to the receiver from the light redirecting means a light attenuating filter of such strength that the average strength of the electrical signal produced by the receiver due to the light reflected from the web is equal to the average strength of the electrical signal due to the light redirected to the receiver from the light redirecting means.

7. A method according to claim 6 wherein the light redirecting means is a reflection means.

8. A method according to claim 7 wherein the light reflection means is a mirror placed so as to protrude beyond either edge of the web on the side of the web remote from the light scanning source.

9. A method according to claim 7 wherein the scanning beam is polarised light and the light reflecting means is a polarised sheet placed beyond the edges of the web and so oriented to attenuate the light reflected therefrom.

10. A method according to claim 7 wherein the light reflecting means is a polished roller which supports the web at the point of scanning.

11. A method according to claim 6 wherein the light redirecting means is a light conducting means.

12. A method according to claim 6 wherein the light attenuating filter is placed in the path of the redirected light.

13. A method according to either claim 6 or claim 12 wherein the light attenuating filter is of the graded density type.

14. A method according to either claim 6 or claim 12 wherein the light attenuating filter comprises two superimposed light polarising sheets, one oriented with respect to the other.

15. A method according to claim 1 wherein light reflected or transmitted by the web is directed to a first light receiver and the light passing the web within the auxiliary scanning zones is directed to a second light receiver, and wherein the output signals of the light receivers are so matched and added that the resulting sum signal remains constant over substantially the whole scanning sweep.

16. A method according to claim 1 wherein a signal is received when a scanning beam crosses an edge of the web.

17. A scanning apparatus for a moving web comprising means for generating a narrow scanning light beam and sweeping the beam across and beyond the edges of the web, a measuring unit including a light receiver generating an electrical output signal corresponding to the light received, means for directing the light reflected or transmitted by the web to said light receiver, optical means for simulating the optical reflection or transmission property of the web for two auxiliary scanning zones adjacent the lateral edges of the web in such manner that the average strength of said electrical output signal remains constant over substantially the whole scanning sweep.

18. An apparatus according to claim 17 wherein the light directing means direct the light reflected or transmitted by the web as well as the light passing the web within said auxiliary scanning zones to said light receiver, and wherein the simulating means is an optical light attenuating element present in the optical path of the light passing the web.

19. An apparatus according to claim 18 wherein the light attenuating element comprises two light polarising sheets mutually oriented.

20. An apparatus according to claim 18 wherein light is received by the receiver from light transmitted by the web wherein the light scanning source is polarised light and the light attenuating element is a polarising sheet.

21. An apparatus according to claim 20 wherein the polarising sheet is arranged in the direction of the scanning light behind the web and extends across the web and the auxiliary scanning zones.

22. An apparatus according to claim 18 wherein light is received by the receiver from light reflected by the web and the light attenuating element is an optical density wedge.

23. An apparatus according to any one of claims 17, 18, or 22 wherein the light is received by the receiver from light reflected by the web and the light reflecting surface is a mirror extending across the web and protruding beyond the edges.

24. An apparatus according to any one of claims 17, 18, or 22 wherein light is received by the receiver from light reflected by the web and the light reflecting surface is a polished roller which supports the web at the point of scan.

25. An apparatus according to claim 17 wherein the measuring unit comprises two light receivers with associated amplifiers and an adder for the output signals of the amplifiers, the light directing means directing light reflected or transmitted by the web to one light receiver and light passing the web within the auxiliary scanning zones to the other light receiver, and the amplifiers being mutually matched so that the sum signal generated by the adder remains constant over substantially the whole scanning sweep.

26. An apparatus according to claim 17 wherein there is provided a web edge detector which comprises an additional light receiver arranged to receive light both from the web and one auxiliary scanning zone.

27. An apparatus according to claim 17 wherein the light source used to generate the light beam is a laser.

28. An apparatus according to claim 17 wherein an oscillating reflector is used to cause the beam to scan across the web.

29. An apparatus according to claim 17 wherein a multi faceted mirroris used to cause the beam to scan across the web.

30. A method of photoelectrically scanning a moving web material which comprises scanning the web with a narrow light beam sweeping across and beyond the edges of the web, directing light reflected or transmitted by the web to a light receiver of a light measuring unit so generating a corresponding electrical signal, and electronically simulating the optical reflexion of transmission property of the web for two auxiliary scanning zones adjacent the lateral edges of the web in such manner that the average strength of said electrical signal remains constant over substantially the whole scanning sweep.

31. A scanning apparatus for a moving web comprising means for generating a narrow scanning light beam and sweeping the beam across and beyond the edges of the web, a measuring unit including a light receiver generating an electrical output signal corresponding to the light received, means for directing the light reflected or transmitted by the web to said light receiver, electronic means for simulating the optical reflection or transmission property of the web for two auxiliary scanning zones adjacent the lateral edges of the web in such manner that the average strength of said electrical output signal remains constant over substantially the whole scanning sweep.

32. A method according to claim 1 wherein the beam is scanned across the web by use of a multi faceted mirror drum.

* * * * *